(12) United States Patent
McDevitt

(10) Patent No.: US 12,369,900 B2
(45) Date of Patent: Jul. 29, 2025

(54) SECURING GRAFT TISSUE IN A BONE TUNNEL AND IMPLEMENTATIONS THEREOF

(71) Applicant: CONMED CORPORATION, Utica, NY (US)

(72) Inventor: Dennis McDevitt, Raleigh, NC (US)

(73) Assignee: CONMED CORPORATION, Utica, NY (US)

( * ) Notice: Subject to any disclaimer, the term of this patent is extended or adjusted under 35 U.S.C. 154(b) by 374 days.

(21) Appl. No.: 16/703,334

(22) Filed: Dec. 4, 2019

(65) Prior Publication Data

US 2020/0107827 A1    Apr. 9, 2020

Related U.S. Application Data

(62) Division of application No. 15/078,368, filed on Mar. 23, 2016, now Pat. No. 10,595,846.

(60) Provisional application No. 62/136,784, filed on Mar. 23, 2015.

(51) Int. Cl.
*A61B 17/04*    (2006.01)
*A61F 2/08*    (2006.01)

(52) U.S. Cl.
CPC ........ *A61B 17/0401* (2013.01); *A61F 2/0811* (2013.01); *A61B 2017/0409* (2013.01); *A61B 2017/0412* (2013.01); *A61B 2017/0424* (2013.01); *A61B 2017/0425* (2013.01); *A61B 2017/0432* (2013.01); *A61B 2017/0438* (2013.01); *A61B 2017/0445* (2013.01); *A61B 2017/0464* (2013.01); *A61F 2002/0835* (2013.01); *A61F 2002/0841* (2013.01); *A61F 2002/0858* (2013.01); *A61F 2002/0882* (2013.01); *A61F 2230/0067* (2013.01); *A61F 2230/0091* (2013.01); *A61F 2250/0039* (2013.01)

(58) Field of Classification Search
None
See application file for complete search history.

(56) References Cited

U.S. PATENT DOCUMENTS

| | | | | |
|---|---|---|---|---|
| 5,236,445 | A * | 8/1993 | Hayhurst | A61B 17/0401 606/232 |
| 5,632,748 | A * | 5/1997 | Beck, Jr. | A61F 2/0811 606/328 |
| 5,935,129 | A * | 8/1999 | McDevitt | A61F 2/0811 606/232 |

(Continued)

*Primary Examiner* — Shaun L David
(74) *Attorney, Agent, or Firm* — Bond, Schoeneck & King, PLLC; Frederick J.M. Price

(57) ABSTRACT

This disclosure describes embodiments of an anchor with a body configured to expand radially outwardly along its entire length. The anchor includes, but is not limited to, a cylindrical body having a longitudinal axis and an inner surface and an outer surface, the inner surface defining a central bore, the cylindrical body having a slot exposing the central bore, the slot having a helical path around the longitudinal axis, wherein the slot is configured to expand so that the cylindrical body changes from a first state to a second state in response to pressure on the inner surface, and wherein an outer diameter of cylindrical body in the second state is larger than the outer diameter of the cylindrical body in the first state.

5 Claims, 17 Drawing Sheets

(56) References Cited

U.S. PATENT DOCUMENTS

| | | | | |
|---|---|---|---|---|
| 6,162,234 | A * | 12/2000 | Freedland | A61F 2/0811 |
| | | | | 606/313 |
| 6,660,008 | B1 * | 12/2003 | Foerster | A61B 17/0401 |
| | | | | 606/232 |
| 2003/0187444 | A1 * | 10/2003 | Overaker | A61B 17/0401 |
| | | | | 606/232 |
| 2007/0005068 | A1 * | 1/2007 | Sklar | A61B 17/0401 |
| | | | | 606/139 |
| 2009/0248068 | A1 * | 10/2009 | Lombardo | A61F 2/0811 |
| | | | | 606/232 |
| 2009/0318964 | A1 * | 12/2009 | Lombardo | A61B 17/0401 |
| | | | | 606/232 |
| 2009/0319043 | A1 * | 12/2009 | McDevitt | A61F 2/08 |
| | | | | 623/13.14 |
| 2010/0228301 | A1 * | 9/2010 | Greenhalgh | A61B 17/744 |
| | | | | 606/313 |
| 2010/0318125 | A1 * | 12/2010 | Gerber | A61B 17/0401 |
| | | | | 606/232 |
| 2011/0071579 | A1 * | 3/2011 | Reach, Jr. | A61B 17/0401 |
| | | | | 411/360 |
| 2011/0112550 | A1 * | 5/2011 | Heaven | A61B 17/0401 |
| | | | | 606/151 |
| 2012/0078298 | A1 * | 3/2012 | Sklar | A61B 17/0401 |
| | | | | 606/232 |
| 2014/0012336 | A1 * | 1/2014 | Biedermann | A61B 17/844 |
| | | | | 606/328 |
| 2014/0148864 | A1 * | 5/2014 | Lacaze | A61B 17/844 |
| | | | | 606/327 |
| 2014/0249579 | A1 * | 9/2014 | Heaven | A61F 2/0811 |
| | | | | 606/232 |

* cited by examiner

SECURING GRAFT TISSUE IN A BONE TUNNEL AND IMPLEMENTATIONS THEREOF

CROSS-REFERENCE TO RELATED APPLICATIONS

The present application is a divisional of and claims priority to and the benefit of U.S. Non-Provisional patent application Ser. No. 15/078,368, filed on Mar. 23, 2016, which claims priority to and the benefit of U.S. Provisional Patent Application No. 62/136,784, filed on Mar. 23, 2015, the entire contents of each are hereby incorporated by reference.

BACKGROUND OF THE INVENTION

1. Field of the Invention

The present disclosure is directed generally to surgical devices with particular discussion about embodiments of an anchor configured to expand to secure graft tissue in a bone tunnel.

2. Description of the Related Art

Many surgical procedures to repair torn or damaged tissue require the surgeon to form a tunnel in a bone or boney member. This bone tunnel serves as a site to anchor graft tissue or sutures. For reconstructive repair of the knee, for example, tunnels penetrate through both the tibia and femur to receive graft tissue and, thus, join the bones together to restore normal functions of the joint.

Anchors are useful to secure the graft tissue in place in the bone tunnel. These anchors can insert into the bone tunnel, often with the graft tissue disposed about the periphery of the anchor and between the anchor and the wall(s) of the bone tunnel. In use, the anchors can be configured to expand radially outwardly to compress the graft tissue against the wall(s).

Radial expansion in many anchors results because the anchor has a body with particular portions that are movable or transitory relative to other portions of the device. The movable portions result from various cuts, slots, and related features in the body of the anchor. In many cases, the body also utilizes materials (e.g., polyethylene) having material properties that allow the movable portions to flex under a load.

Description of the Related Art Section Disclaimer: To the extent that specific patents/publications/products are discussed above in this Description of the Related Art Section or elsewhere in this Application, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

SUMMARY OF THE INVENTION

Embodiments of the present invention recognize that there are potential problems and/or disadvantages with the conventional suture anchors such as not including a body that expands radially outwardly along its entire length. Therefore, a need exists for anchors with a body configured to expand. Various embodiments of the present invention may be advantageous in that they may solve or reduce one or more of the potential problems and/or disadvantages discussed herein.

The present disclosure is directed to an inventive configuration, structure, and resulting function of an anchor to secure graft tissue. Various embodiments herein are directed to an anchor, including, but not limited to: an elongate body having a distal end, a proximal end, and a longitudinal axis extending therebetween, the elongate body having an outer surface and an inner surface, the inner surface defining a bore aligned with and extending along the longitudinal axis, the elongate body comprising a slot penetrating into the outer surface towards the longitudinal axis, the slot forming a path circumscribing the longitudinal axis.

According to an alternative embodiment, the anchor, includes, but is not limited to a cylindrical body having an outer diameter that increases from a distal end to a proximal end, the cylindrical body having a longitudinal axis and a central bore aligned therewith, the central bore forming an inner surface, the cylindrical body having a slot exposing the central bore, the slot having a helical path around the longitudinal axis, wherein the slot is configured so that the cylindrical body changes from a first state to a second state in response to pressure on the inner surface of the central bore, and wherein the outer diameter of cylindrical body in the second state is larger than the outer diameter of the cylindrical body in the first state at both the distal end and the proximal end.

According to another aspect, a system for securing graft tissue in a bone tunnel includes, but is not limited to, an anchor member comprising a body having a distal end, a proximal end, and a central bore extending therebetween, the central bore defining a longitudinal axis, the body incorporating a slot that penetrates from an outer surface through an inner surface of the central bore, the slot having a first end and a second end proximate the distal end and the proximal end, respectively, the slot traversing the body in both a circumferential and longitudinal direction; and a movable member configured to insert into the central bore of the anchor member, wherein the body is configured to expand radially with the movable member in position in the central bore entirely along a length as measured between two planes, one each disposed at the distal end and the proximal end, parallel to one another, and perpendicular to the longitudinal axis.

According to an alternative embodiment, a system for securing graft tissue in a bone tunnel includes, but is not limited to, an anchor member comprising a body having a distal end, a proximal end, and a central bore extending therebetween, the central bore defining a longitudinal axis, the body incorporating a slot that penetrates from an outer surface through an inner surface of the central bore, the slot having a first end and a second end proximate the distal end and the proximal end, respectively, the slot traversing the body in both a circumferential and longitudinal direction; a movable member configured to insert into the central bore of the anchor member, wherein the body is configured to expand radially with the movable member in position in the central bore entirely along a length as measured between two planes, one each disposed at the distal end and the proximal end, parallel to one another, and perpendicular to the longitudinal axis; and a cannulated shaft having a first engagement region configured to engage the movable member, the cannulated shaft configured to receive an inserter tooling therethough, the inserter tooling having a second engagement region configured to engage the anchor member, wherein rotating the cannulated shaft inserts the movable member into the central bore of the anchor member.

According to an alternative embodiment, a system for securing graft tissue in a bone tunnel includes, but is not limited to, an anchor member comprising a body having a distal end, a proximal end, and a central bore extending therebetween, the central bore defining a longitudinal axis, the body incorporating a slot that penetrates from an outer surface through an inner surface of the central bore, the slot having a first end and a second end proximate the distal end and the proximal end, respectively, the slot traversing the body in both a circumferential and longitudinal direction; a movable member configured to insert into the central bore of the anchor member, wherein the body is configured to expand radially with the movable member in position in the central bore entirely along a length as measured between two planes, one each disposed at the distal end and the proximal end, parallel to one another, and perpendicular to the longitudinal axis; and a cannulated shaft having a first engagement region configured to engage the movable member, the cannulated shaft configured to receive an inserter tooling therethough, the inserter tooling having a second engagement region configured to engage the anchor member, wherein rotating the cannulated shaft inserts the movable member into the central bore of the anchor member.

BRIEF DESCRIPTION OF THE DRAWINGS

The present invention will be more fully understood and appreciated by reading the following Detailed Description in conjunction with the accompanying drawings. The accompanying drawings illustrate only typical embodiments of the disclosed subject matter and are therefore not to be considered limiting of its scope, for the disclosed subject matter may admit to other equally effective embodiments.

Reference is now made briefly to the accompanying drawings, in which.

Figure 1:
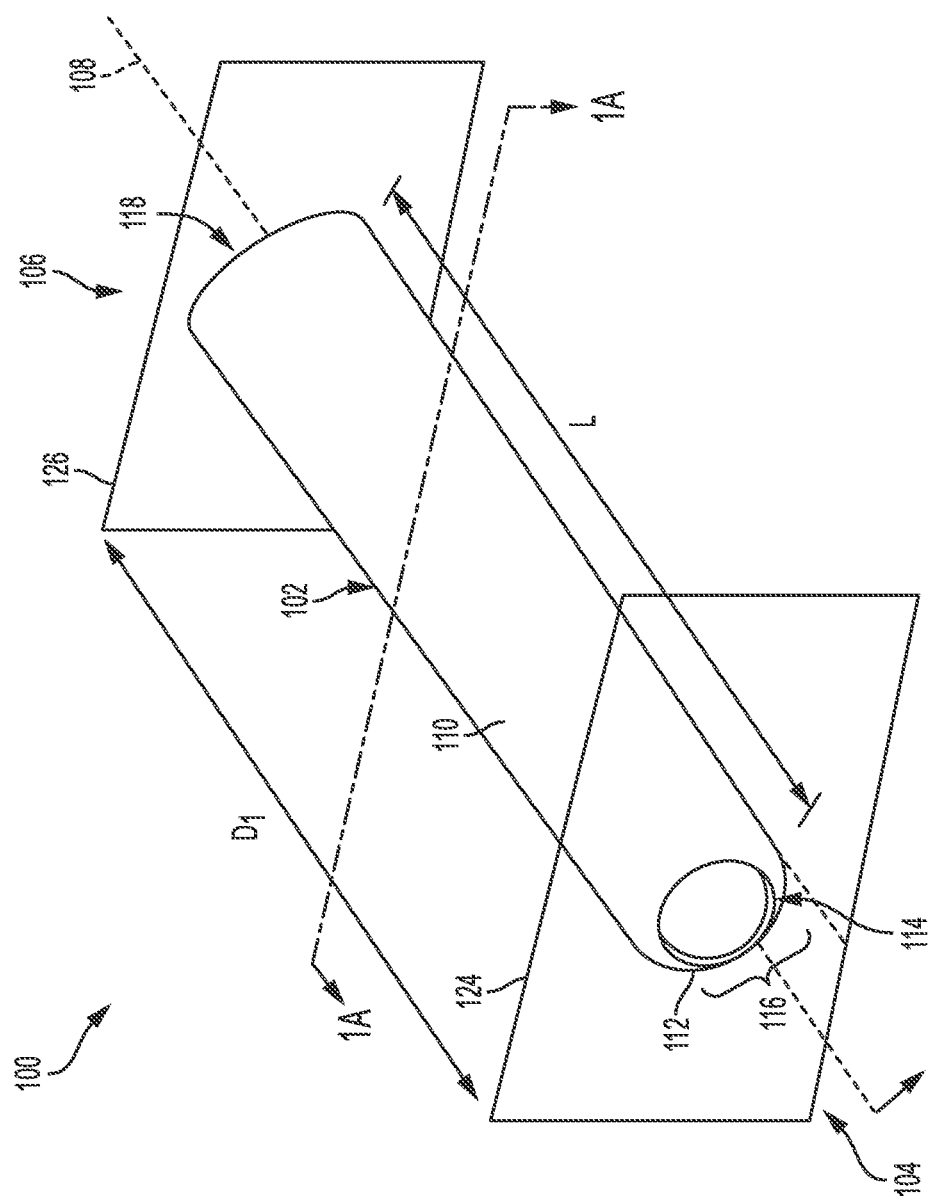
FIG. 1 is a schematic diagram of a perspective view of an exemplary embodiment of an anchor for securing graft tissue in a bone tunnel in accordance with an embodiment.

Where applicable like reference characters designate identical or corresponding components and units throughout the several views, which are not to scale unless otherwise indicated. Moreover, the embodiments disclosed herein may include elements that appear in one or more of the several views or in combinations of the several views.

DETAILED DESCRIPTION

Referring now to FIG. 1, there is shown a schematic diagram of an exemplary embodiment of an anchor 100. The embodiment has an elongate body 102 with a first body end 104, a second body end 106, and a longitudinal axis 108 extending therebetween. The elongate body 102 has an outer surface 110 and an inner surface 112 that circumscribes the longitudinal axis 108 to form a bore 114 (also, "lumen 114"). The bore 114 can penetrate through the elongated body 102 to form one or more openings (e.g., first opening 116 and a second opening 118), one disposed at each end 104, 106 of the elongate body 102.

As also shown in FIG. 1, the elongate body 102 resides between a pair of longitudinally-spaced transverse planes (e.g., a first longitudinally-spaced transverse plane 124 and a second longitudinally-spaced transverse plane 126). The transverse planes 124, 126 are parallel to one another and perpendicular (or transverse) to the longitudinal axis 108. In FIG. 1, the transverse planes 124, 126 are spaced apart from one another along the longitudinal axis 108 by a longitudinal distance D1. In one example, the longitudinal distance D1 corresponds at least with a length L of the elongate body 102 as measured from the ends 104, 106.

Figure 1A:
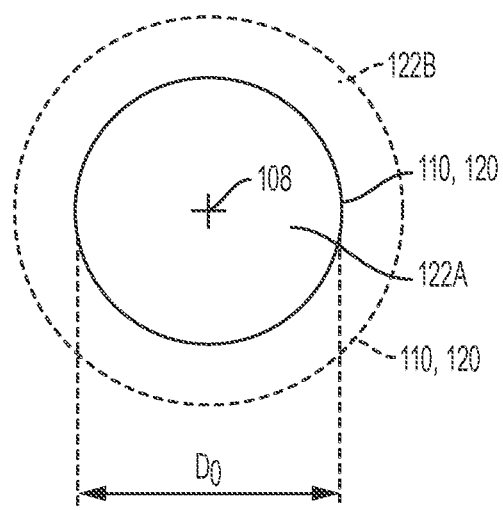
FIG. 1A depicts an elevation view of a cross-section of the anchor of FIG. 1 in accordance with an embodiment.

Referring now to FIG. 1A, there is shown a schematic diagram of an elevation view of the cross-section of the anchor 100 taken at line 1A-1A of FIG. 1. The elongate body 102 has an outer boundary 120 that defines a cross-sectional area 122. The outer boundary 120 may be defined by one or more outer dimensions $D_O$. In one example, the outer dimensions $D_O$ and the outer boundary 120, generally, correspond with the outer surface 110 and/or otherwise correspond with the shape of the elongate body 102 at its cross-section. This shape may be circular or annular, as shown, in which the outer dimension $D_O$ defines an outer diameter for the circular cross-section; however, this disclosure contemplates that the elongate body 102 can assume other shapes (e.g., square, rectangular, elliptical, diamond, etc.). In one implementation, radial expansion of the elongate body 102 increases the cross-sectional area from a first cross-sectional area 122A (in an un-deployed state) to a second cross-sectional area 122B (in a deployed state), which is larger the first cross-sectional area 122A.

With reference to both FIGS. 1 and 1A, the elongate body 102 is configured for the cross-sectional area 122 to increase along the entire length L in response to pressure on the inner surface 112. This configuration effectively expands the cross-sectional area 122 of the elongate body 102 radially outwardly in its entirety along the longitudinal axis 108. The length L of elongate body 102 may remain constant, or the same, in both the un-deployed state and the deployed state. The increase in cross-sectional area 122 changes the volume of the elongate body 102 from a first volume (in the un-deployed state) to a second volume (in the deployed state). In one example, the second volume is larger than the first volume.

Figure 2:
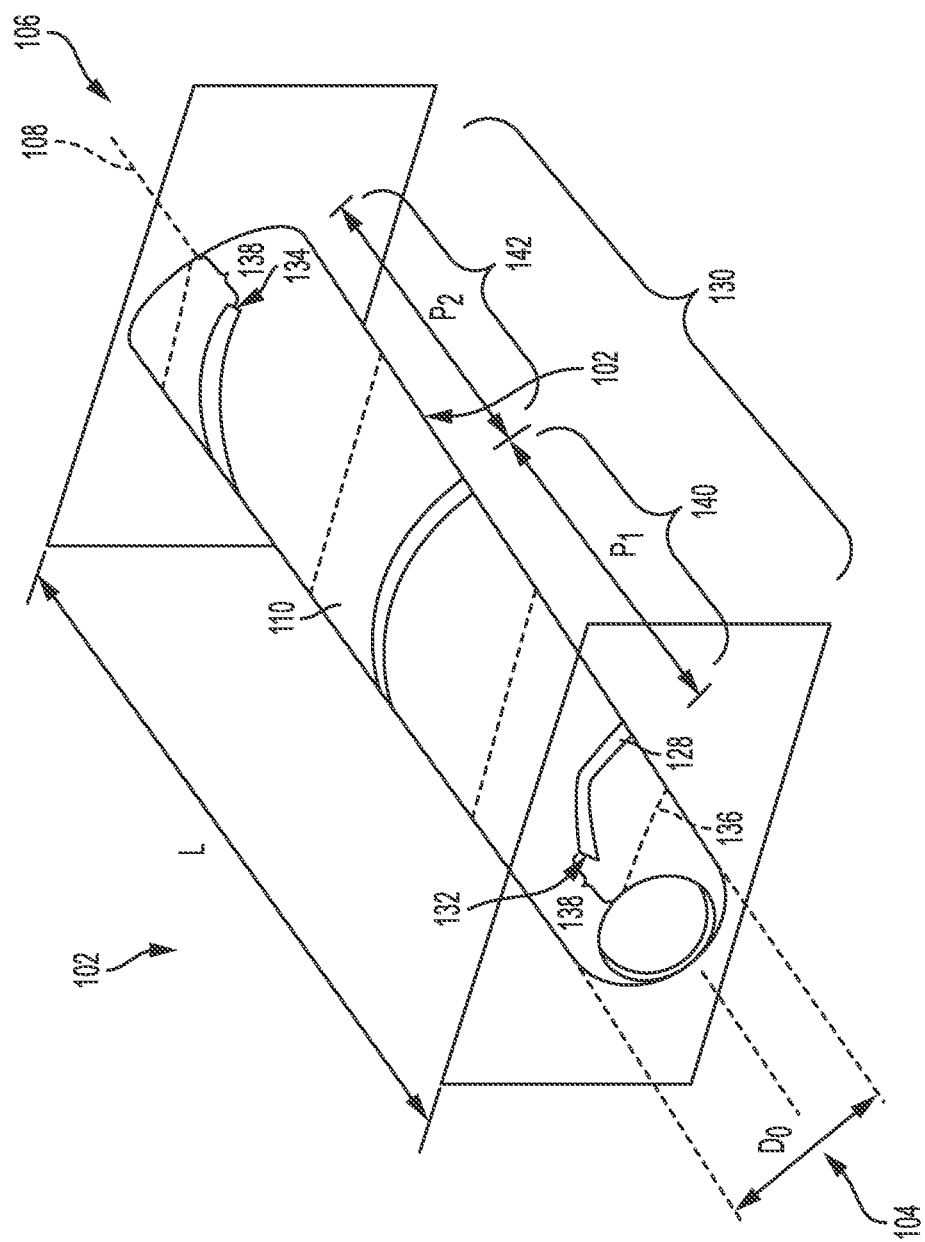
FIG. 2 depicts a schematic diagram of an example of the anchor of FIG. 1 in a configuration that allows radial expansion for securing graft tissue in the bone tunnel in accordance with an embodiment.
Figure 8:
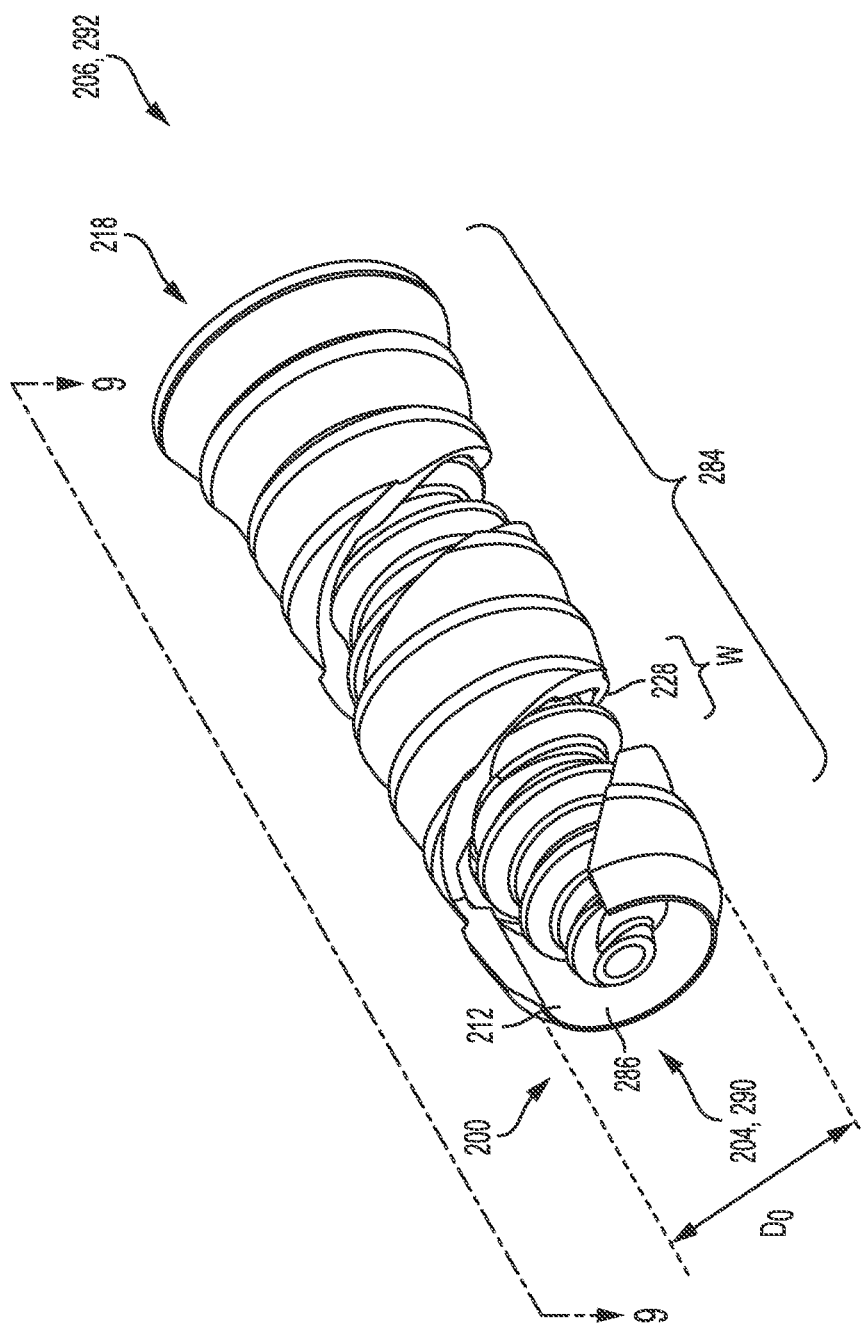
FIG. 8 depicts a perspective view of the anchoring system of FIG. 7 in assembled form in accordance with an embodiment.
Figure 9:
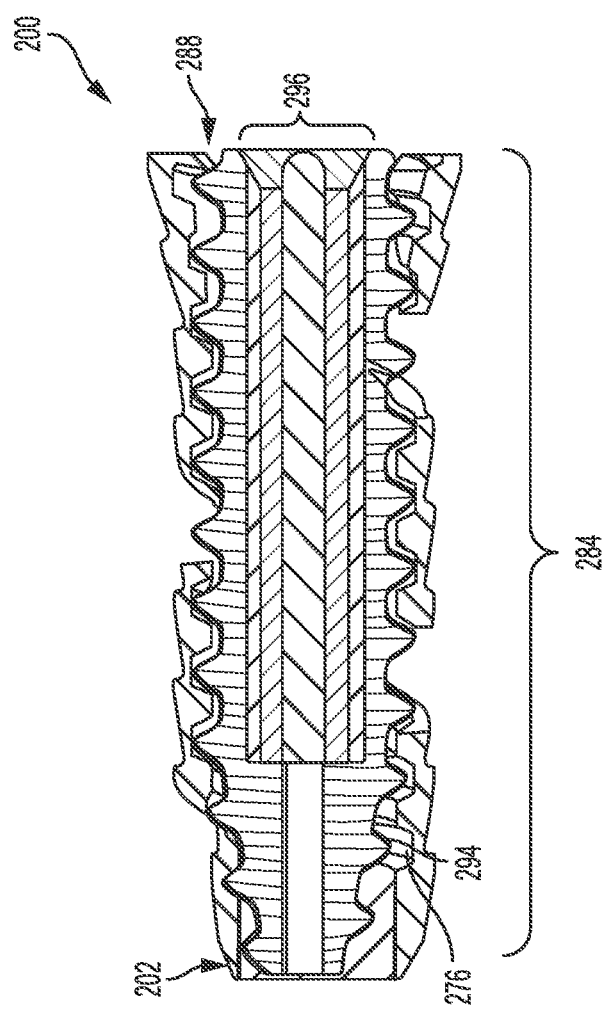
FIG. 9 depicts an elevation view of a cross-section of the anchoring system of FIG. 8 in accordance with an embodiment.

Expansion of the elongate body 102 is useful to secure graft tissue in a bone tunnel. In one implementation, a screw or like movable element can be used to apply the pressure, as noted more herein. The movable element can change the elongate body 102 from the un-deployed state (shown in FIGS. 1 and 2) to the deployed state (FIG. 2 and also FIGS. 8 and 9 below). For circular and/or annular cross-sections, the elongate body 102 can assume a first outer diameter in the un-deployed state to insert into the bone tunnel with the outer surface 110 adjacent the graft tissue. Transition to the deployed state expands the elongate body 102 to a second outer diameter to compress the graft tissue against the walls of the bone tunnel. In some implementations, the elongate body 102 can also engage the walls, thus securing the anchor 100 firmly in place in the bone tunnel.

Referring now to FIG. 2, there is shown a first configuration for the elongate body 102 to allow for the expansion from the first outer dimension to the second outer dimension. The elongate body 102 includes a slot 128 of width W. The slot 128 forms a path 130 with a pair of ends (e.g., a first path end 132 and a second path end 134). The path 130 is configured to circumscribe the longitudinal axis 108 and also traverses the elongate body 102 longitudinally between the ends 104, 106. This configuration forms a contact surface on the elongate body 102, as identified generally by the dashed line enumerated 136. The path ends 132, 134 can reside proximate the body ends 104, 106. In one embodiment, the path ends 132, 134 are spaced apart from one or both body ends 104, 106. Such spacing can form a first material connection 138 (also "first frangible connection 138") to maintain the elongate body 102 in its un-deployed state. In use, the expansion of the elongate body 102 from the first outer dimension to the second outer dimension breaks the first material connections 138 in response to pressure on the inner surface 112. The second outer dimension positions the contact surface 136 (relative to the longitudinal axis 108) to compress against graft tissue and/or wall of the bone tunnel.

The slot 128 is configured to penetrate into the material of the elongate body 102. In one example, the slot 128 penetrates completely, from the outer surface 110 through the inner surface 112, to expose the bore 114 along the entire path 130. In other examples, the slot 128 does not penetrate completely. These examples can include a thin material section or "bridge" across the width W. The bridge may extend along the entire path 130 or, as noted more below, may extend only partially in the form of one or more bridges along the path 130.

As also shown in FIG. 2, the path 130 has geometry with one or more turns (e.g., a first turn 140 and second turn 142). The turns 140, 142 correspond with a complete revolution of the slot 128 about the longitudinal axis 108. The turns 142, 144 also have a pitch (e.g., a first pitch P1 and a second pitch P2), respectively. Values for the pitch P1, P2 are preferably less than the overall length L of the elongate body 102. In one example, these values are equal, e.g., the value for the first pitch P1 is the same as the value for the second pitch P2.

The geometry of the path 130 prepares the elongate body 102 to expand substantially uniformly along the length L. This geometry can embody a curve (also "helix", "helical," or "spiral") that winds around the longitudinal axis 108. The number of turns 140, 142 can depend on the pitch P1, P2 and the length L of the elongate body 102, although material properties, desired expansion (e.g., the second outer dimension), and other factors may weigh into the configuration of the path 130 and the slot 128, generally. For example, the pitch can increase and decrease longitudinally (from pitch P1 to pitch P2) to allow more or less turns 140, 142 to fit onto the elongate body 102. It is expected that some experimentation may need to balance the capabilities of the anchor 100 to change from the first state to the second state with the physical properties of the device(s) as noted herein.

The helical geometry is at least advantageous because it allows construction of the elongate body 102 with harder and/or less flexible materials. In general, the construction may utilize plastics and polymers. However, because the helical geometry distributes deflection of the elongate body 102 over substantially the entire length L, constructions for the elongate body 102 can utilize polyether ether ketone (PEEK) and similar materials having a Young's modulus of at least about 4.5 GPa or greater. In the deployed state, these materials can afford the anchor 100 with more durable engagement with graft tissue and wall(s) of the bone tunnel, where applicable.

Another advantage of the helical geometry is at least to increase contact between the elongate body 102 and graft tissue in the bone tunnel. The helical geometry arranges the contact surface 136 annularly around the longitudinal axis 108. This arrangement effectively allows the anchor 100 to engage graft tissue around its entire periphery, e.g., contact can occur with at least one graft tissue in 360° about the longitudinal axis 108. In one implementation, the contact surface 136 circumscribes the longitudinal axis 108 continuously from the first end 102 to the second end 104.

Figure 3:
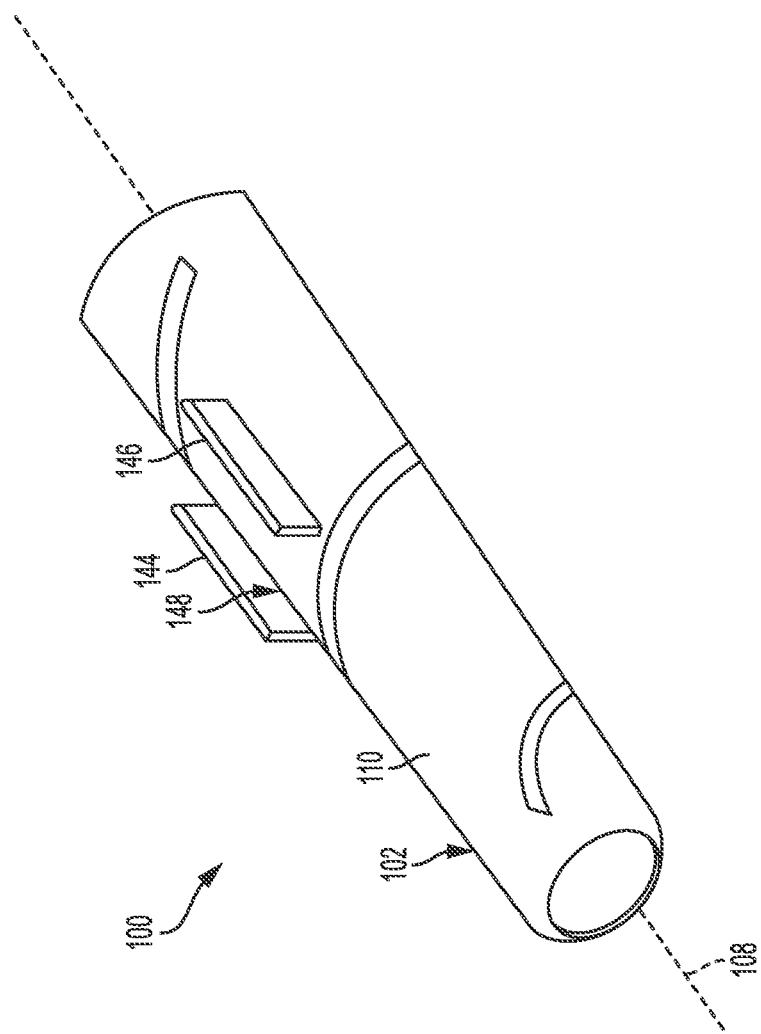
FIG. 3 depicts a schematic diagram of an example of the anchor of FIG. 1 in a configuration that aligns graph tissue on the anchor in accordance with an embodiment.

Referring now to FIG. 3, there is shown a second configuration for the elongate body 102. In this second configuration, one or more protrusions (e.g., a first protrusion 144 and a second protrusion 146) populate the outer surface 110 of the elongated body 102. Each of the protrusions 144, 146 have a body that extends longitudinally along and the longitudinal axis 108 and radially away from the outer surface 110. The protrusions 144, 146 are spaced annularly apart from one another to form a graft pathway 148. In use, the graft pathway 148 can receive graft tissue. This feature can align the graft tissue with the anchor 100 to better facilitate contact and compression by the outer surface 110 (FIG. 2) against the wall(s) of the bone tunnel.

Figure 4:
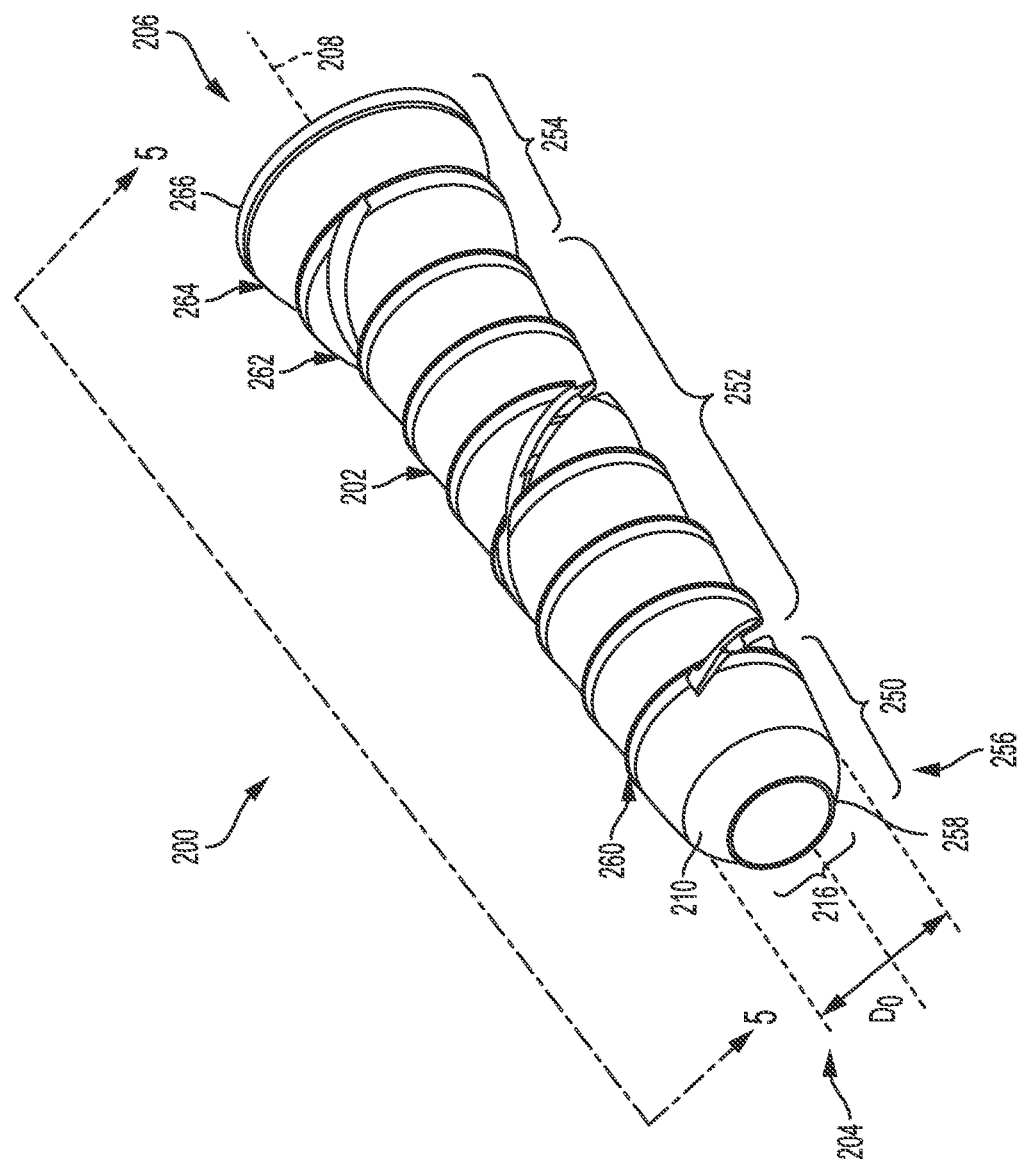
FIG. 4 depicts a perspective view of an exemplary embodiment of an anchor for securing graft tissue in the bone tunnel in accordance with an embodiment.

Referring now to FIG. 4, there is shown a perspective view of an exemplary embodiment of an anchor 200 in its un-deployed state. The elongate body 202 forms a cylinder or a generally cylindrical shape. This cylinder can be manufactured monolithically from the selected material (e.g., PEEK), potentially by turning a single piece or billet of the selected material and/or by molding or casting as desired.

The cylinder has a number of sections (e.g., a first section 250, a second section 252, and a third section 254). The sections 250, 252, 254 correspond with the geometry of the elongate body 202. Moving from the first end 204 to the second end 206, the first section 250 includes a nose portion 256. The nose portion 256 can form a distal facing surface 258 that circumscribes the first opening 216. The distal facing surface 258 can be flat and generally perpendicular to the longitudinal axis 208 to form the nose portion 256 as blunt or non-pointed. The outer surface 210 extends from the distal facing surface 258, tapering outwardly away from the longitudinal axis 208. This part of the outer surface 210 can be smooth or relative free of protuberances, as shown, to facilitate insertion of the anchor 200 into position adjacent graft tissue in the bone tunnel.

The second section 252 incorporates a majority (e.g., greater than 50%) of the length L of the elongate body 202. In the second section 252, a first engagement member 260 populates the elongate body 202. The first engagement member 260 forms the outer surface 210 into one or more first protrusions that reside adjacent and/or abut one another along the longitudinal axis 208. The first protrusions are annular and circumscribe the longitudinal axis 208, as shown. However, this disclosure does contemplate configurations in which one or more of the annular protrusions extend only partially (e.g., less than 360°) around the longitudinal axis 208.

In the third section 254, the outer diameter $D_O$ of the elongate body 202 increases relative to the outer diameter $D_O$ in the second section 252. The elongate body 202 can include a second engagement member 262 and a flared or flange portion 264. Like the first engagement member 260, the second engagement member 262 can form the outer surface 210 into one or more second protrusions, preferably annular and either fully or partially circumscribing the longitudinal axis 208. The second protrusions can be larger than the first protrusions in keeping with the flared configuration of the elongate body 202.

The flange portion 264 is configured to manage depth of the elongate body 202 into the bone tunnel. In one embodiment, the flange portion 264 resides adjacent to the second protrusion and has a flanged edge 266. The flange portion 264 forms the outer surface 210 to taper outwardly away from the longitudinal axis 208. The flanged edge 266 can circumscribe the longitudinal axis 208, defining a value for the outer diameter $D_O$ of the elongate body 202 that may be larger than the diameter of the bone tunnel.

Figure 5:
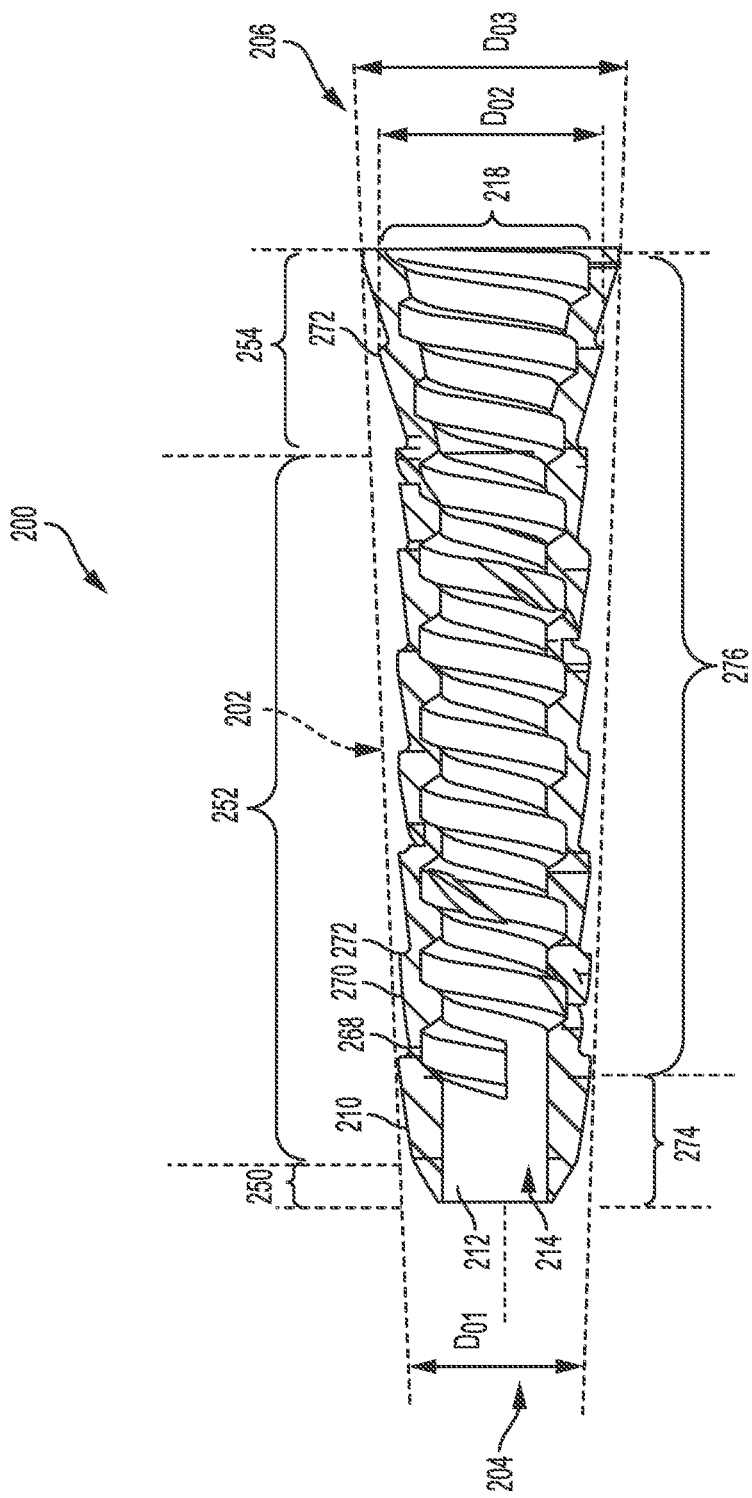
FIG. 5 depicts an elevation view of a cross-section of the anchor of FIG. 4 in accordance with an embodiment.

Referring now to FIG. 5, there is shown an elevation view of the cross-section of the anchor 200 taken at line 5-5 of FIG. 4. On the outer surface 210, the elongate body 202 has a fillet 268 disposed on the proximal side of one or both of the first and second protrusions. The fillet 268 integrates with a tapered surface 270 that terminates at an outer protrusion edge 272. The outer peripheral edge 272 can define the outer dimension $D_O$ for the outer surface 210 in each of the sections 252, 254. In one implementation, the outer dimension $D_O$ has a first value ($D_{O1}$) in the second section 252. This first value $D_{O1}$ can remain constant along the longitudinal axis 208 (within certain applicable manufacturing tolerances). The outer dimension $D_O$ has a second value ($D_{O2}$) at the outer peripheral edge 272 of the second annular protrusion. The second value $D_{O2}$ can be larger than the first value $D_{O1}$. The outer dimension has a third value ($D_{O3}$) at the flanged edge 266 that can be larger than the second value $D_{O2}$ and the first value $D_{O1}$.

As also shown in FIG. 5, the inner surface 212 has a flat portion 274 generally devoid of protuberances or other protrusions. The wall of the bore 214 in the flat portion 274 can extend parallel to the longitudinal axis 208. Adjacent the flat portion 274 and spaced apart from the first end 204, the inner surface 212 incorporates a threaded portion 276 with threads and/or like engagement feature. These threads can extend along the longitudinal axis 208 to terminate at the second opening 218 of the bore 214. Examples of the threads in the threaded portion 276 can be configured as ACME threads, although this disclosure does contemplate other thread configurations (e.g., National Pipe Thread (NPT), etc.).

Figure 6:
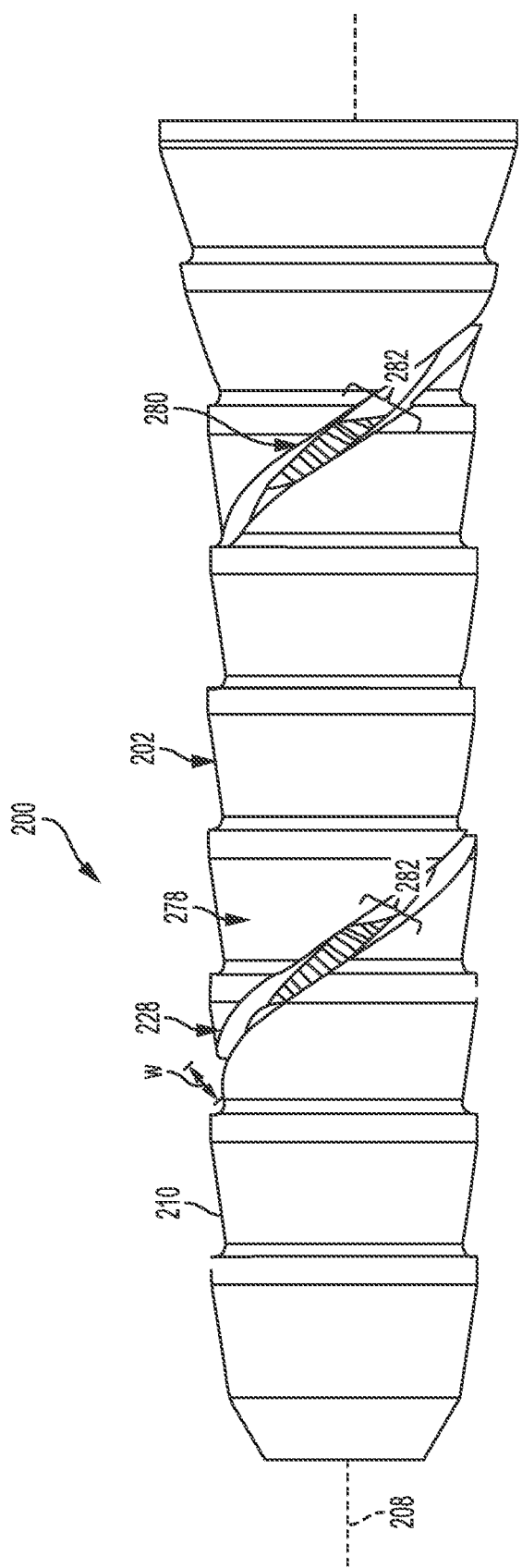
FIG. 6 depicts an elevation view of the side of the anchor of FIG. 4 in a first position that is offset annularly about a longitudinal axis of the anchor in accordance with an embodiment.

Referring now to FIG. 6, there is shown an elevation view of a side of the anchor 200 in a first position that is offset annularly about the longitudinal axis 208. The elongate body 202 includes one or more bridges (e.g., a first bridge 278 and a second bridge 280), demarcated by hatching for clarity. The bridges 278, 280 embody material that spans the width W of the slot 228. This material forms a second material connection 282 to maintain the elongated body 202 in its un-deployed state. The second material connection 282 may reside proximate the inner surface 212 (FIG. 5) as manufacturing techniques are likely to most easily form the slot 228 by removing material from the outer surface 210 inwardly towards the inner surface 212 (FIG. 5). In one implementation, the second material connection 282 is sized and configured to be breakable (or frangible) under load consistent with the pressure on the inside surface 212 (FIG. 5) that causes the anchor 100 to change from its un-deployed state to its deployed state.

Figure 7:
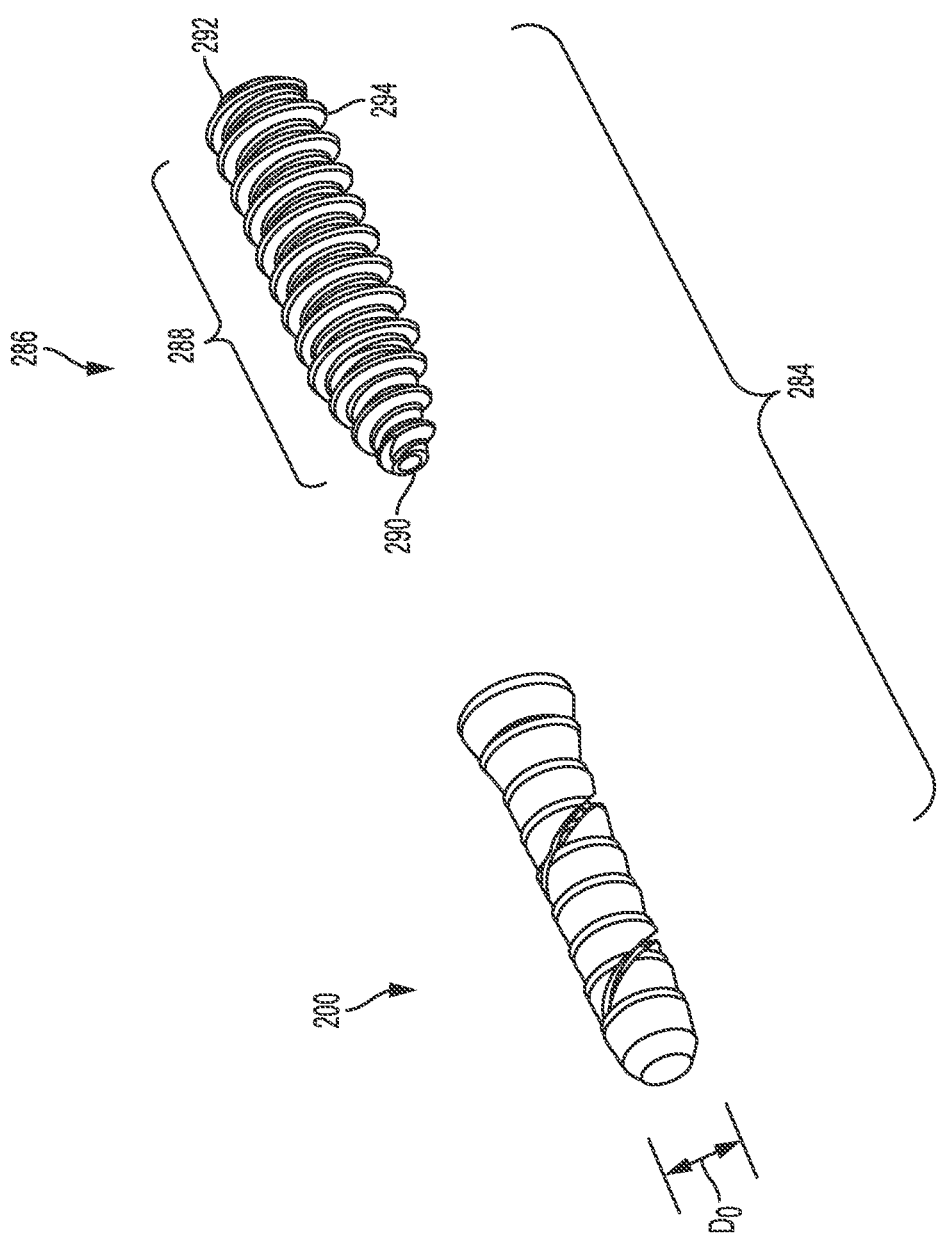
FIG. 7 depicts a perspective view of the anchor of FIG. 4 as part of an anchoring system shown in exploded form in accordance with an embodiment.

Referring now to FIG. 7, there is shown a perspective view of the anchor 200 as part of an anchoring system 284 ("system 284") for securing graft tissue in a bone tunnel. The system 284 is shown in exploded form. In addition to the anchor 200, the system 284 includes a movable member 286. Use of the movable member 286 changes the anchor 200 from its un-deployed state to its deployed state. In one implementation, the movable member 286 has a body 288 with a distal end 290 and a proximal end 292. The body 288 is also configured with threads 294, preferably complimentary with the threads in the threaded portion 276 (FIG. 5) of the elongate body 202. The threads 294 allow the movable member 286 to transit the elongate body 202 of the anchor 200.

Referring now to FIGS. 8 and 9, there is shown the system 284 in assembled form with the anchor 200 in its deployed state. FIG. 8 provides a perspective view of the system 284. FIG. 9 illustrates an elevation view of the cross-section of the system 284 taken at line 9-9 of FIG. 8. In FIG. 8, the distal end 290 of the movable member 286 is in position proximate the first end 204 of the elongate body 202. The threads 294 on the movable member 286 are configured with dimensions (e.g., outer diameter) to apply pressure on the inner surface 212. The pressure causes the elongate body 202 to expand from the un-deployed state (FIG. 7) to the deployed state as evidenced, for example, by the change in the width W of the slot 228, i.e., from a first width in the un-deployed state to a second width in the deployed state, and the change in the outer diameter $D_O$ from a first diameter in the un-deployed state (FIG. 7) to a second diameter in the deployed state (FIG. 8), which is larger than the first diameter. The expansion compresses graft tissue against the surrounding wall(s) of the bone tunnel.

As best shown in FIG. 9, engagement of the threads 294 with the threads in the threaded portion 276 advance the movable member 286 into the elongate body 202. In one embodiment, the movable member 286 can include a tooling feature 296 that penetrates into the body 288 in a direction from the proximal end 292 to the distal end 290. The tooling feature 296 can comprise a bore that extends at least partially into the length of the body 288. This bore can be configured with slots, groove, and/or like depressions. These depressions can receive complimentary features on insertion tooling during a surgical implementation. The surgeon can use the insertion tooling to drive the movable member 286 into the elongate body 202, as noted more below.

Figure 10:
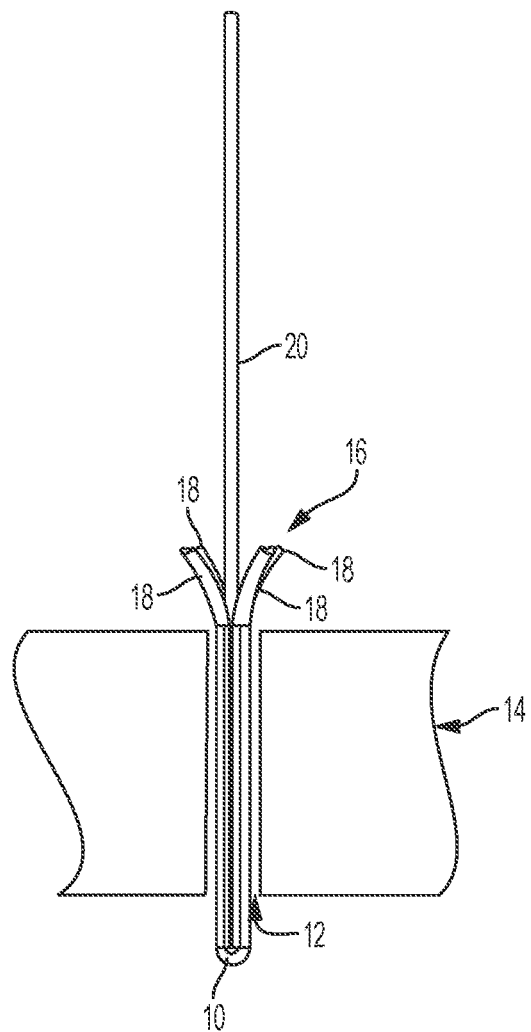
FIG. 10 depicts an elevation view of a surgical implementation in a first stage for deploying an exemplary embodiment of an anchor and an example of an anchoring system for securing graft tissue in a bone tunnel in accordance with an embodiment.

Referring now to FIGS. 10, 11, 12, and 13, there is shown a surgical implementation that uses an exemplary embodiment of an anchor 300 to secure graft tissue in a bone tunnel. Referring first to FIG. 10, the surgical implementation is configured to secure graft tissue 10 inside of a bone tunnel 12 formed in a boney member 14. During the surgery, the surgeon applies force to free ends 16 of legs 18 on the graft tissue 10. This force draws the graft tissue 10 into position inside of the bone tunnel 12. In many implementations, the surgeon will retain some amount of residual tension on the legs 18. The surgeon may insert a guide pin 20 into the bone tunnel 12 on the interior of the legs 18. The guide pin 20 can penetrate at least partly into the bone tunnel 12, and preferably to a depth in the bone tunnel 12 suitable for the anchor 300 (FIGS. 11, 12, 13, and 14) to embed fully into the boney member 14.

Figure 11:
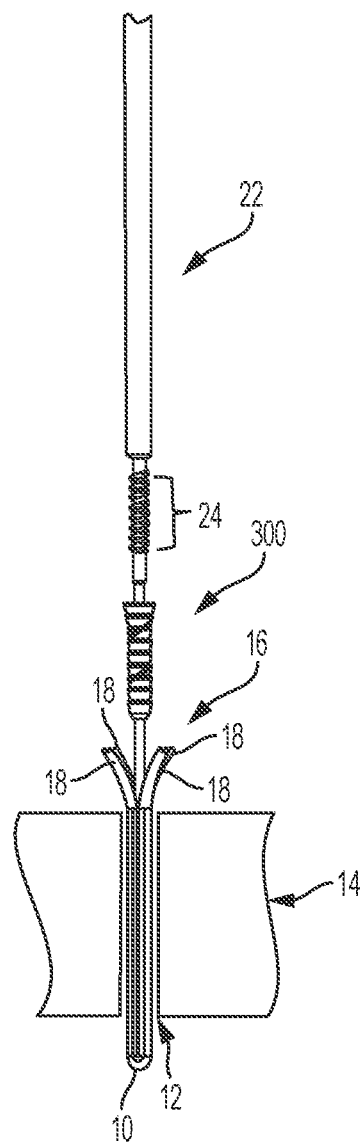
FIG. 11 depicts an elevation view of the surgical implementation of FIG. 10 in a second stage in accordance with an embodiment.

As shown in FIG. 11, the surgeon can use inserter tooling 22 to place the anchor 300 into the bone tunnel 12. The inserter tooling 22 may be cannulated to receive the guide pin 20. The inserter tooling 22 can have a first engagement region 24 configured to engage the anchor 300. For example, the first engagement region 24 may have threads to match threads in the threaded portion 276 (FIG. 5) on the interior of the anchor 300. This configuration is beneficial because the matching threads (or the first engagement region 24, generally) provide positive engagement to facilitate insertion of the anchor 300. The surgeon can forego direct pressure on the inserter tooling 22 in the direction of bone tunnel 12. Engagement between the anchor 300 and the inserter tooling 22 at the first engagement region 24 is sufficient to require the surgeon only to push the anchor 300 into position between the legs 18 of the graft tissue 10. As an added benefit, this engagement also allows the surgeon to back-out and remove the anchor 300 from the bone tunnel 12 after initial placement in between the legs 18 of the graft tissue 10.

Figure 12:
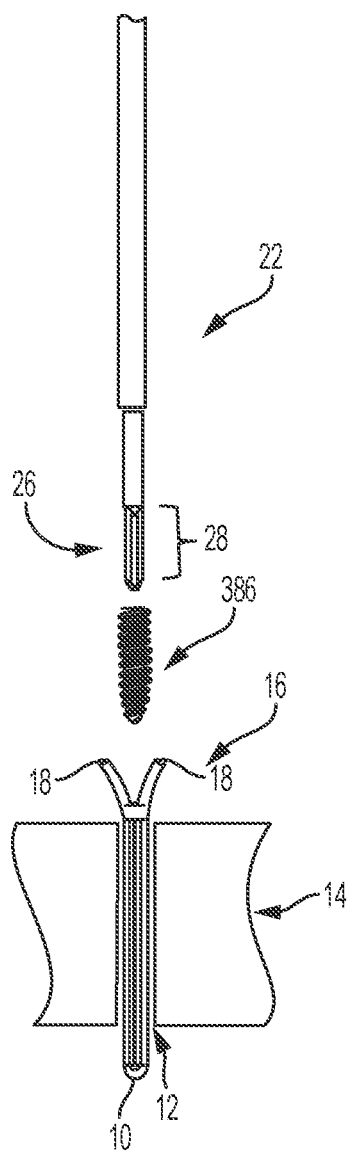
FIG. 12 depicts an elevation view of the surgical implementation of FIG. 10 in a third stage in accordance with an embodiment.

FIG. 12 depicts the surgical implementation with the anchor 300 in position in the bone tunnel 12 and out of view in the diagram. With the guide pin 20 (FIGS. 10 and 11) withdrawn, the surgeon can use inserter tooling 22 to place the movable element 386 into the anchor 300. The inserter tooling 22 may have a second engagement region 26 that is configured to engage the movable element 386. This configuration may implement a tip 28 with features that match the tooling feature 296 (FIG. 9) on the movable element 386.

Figure 13:
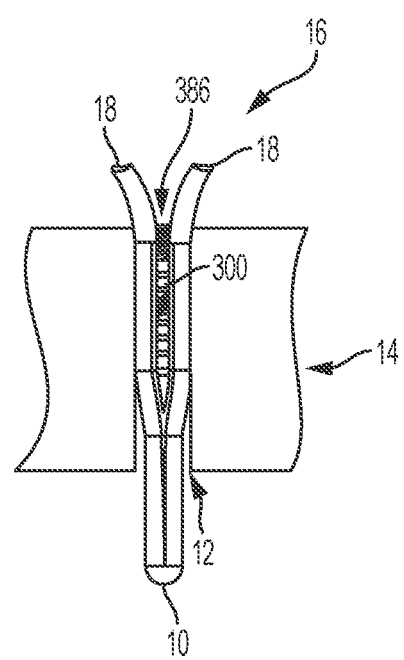
FIG. 13 depicts an elevation view of the surgical implementation of FIG. 10 in a fourth stage in accordance with an embodiment.

FIG. 13 illustrates the surgical implementation with the anchor 300 in its deployed state. Using the inserter tooling 22 (FIG. 12), the surgeon can rotate the movable element 386 into position in the anchor 300. The movable element 386 expands the anchor 300 from its first outer dimension to its second outer dimension. The second outer dimension urges the contact surface 136 (FIG. 2) radially outward and in contact with the graft tissue 10. The radial expansion compresses the graft tissue 10 against the contact surface and the walls of the tunnel 12. As noted above, the flanged end 264 (FIG. 4) can stop (or prevent) movement of the anchoring system 384 further into the bone tunnel 12 when the flanged end 264 (FIG. 4) is at or proximate the proximal opening of the bone tunnel 12.

Figure 14:
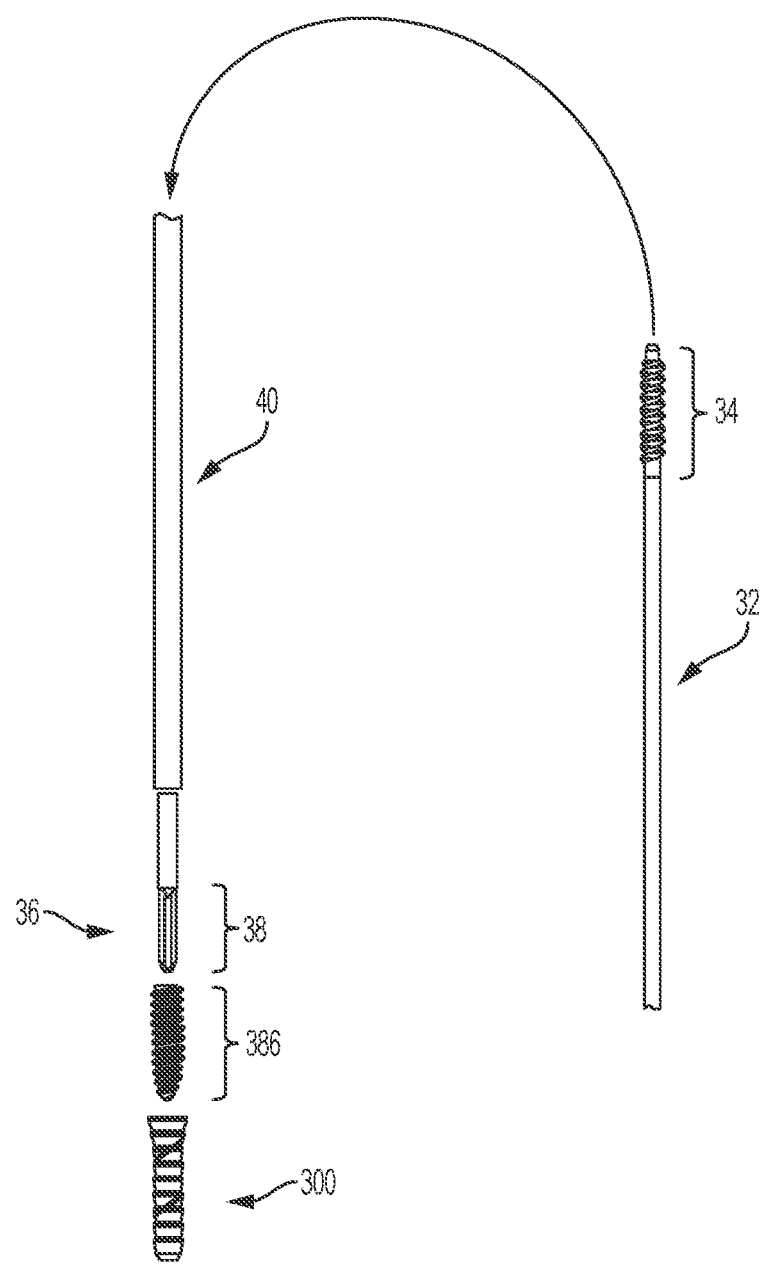
FIG. 14 depicts an exploded view of an alternative inserter tooling coupled with the cannulated shaft of a surgical instrument in accordance with an embodiment.
Figure 15:
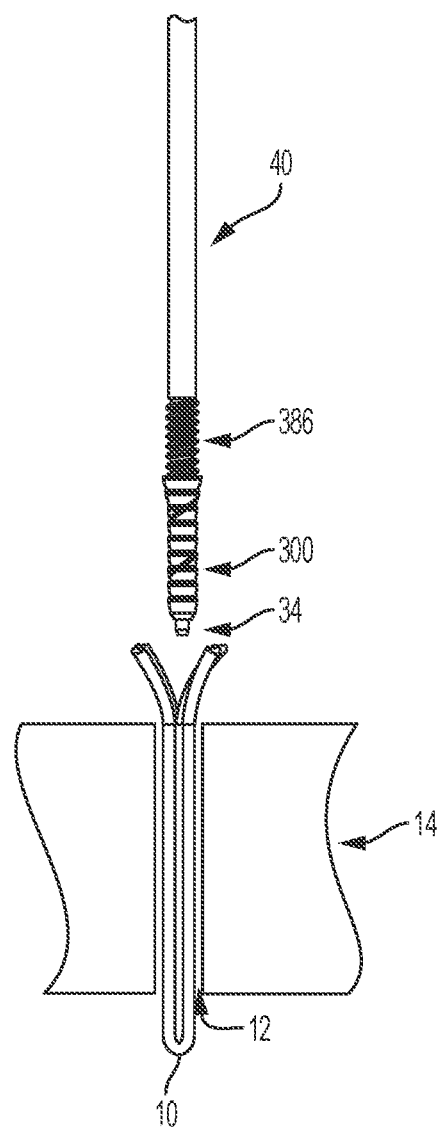
FIG. 15 depicts an elevation view of an alternative embodiment of the surgical implementation in accordance with an embodiment.
Figure 16:
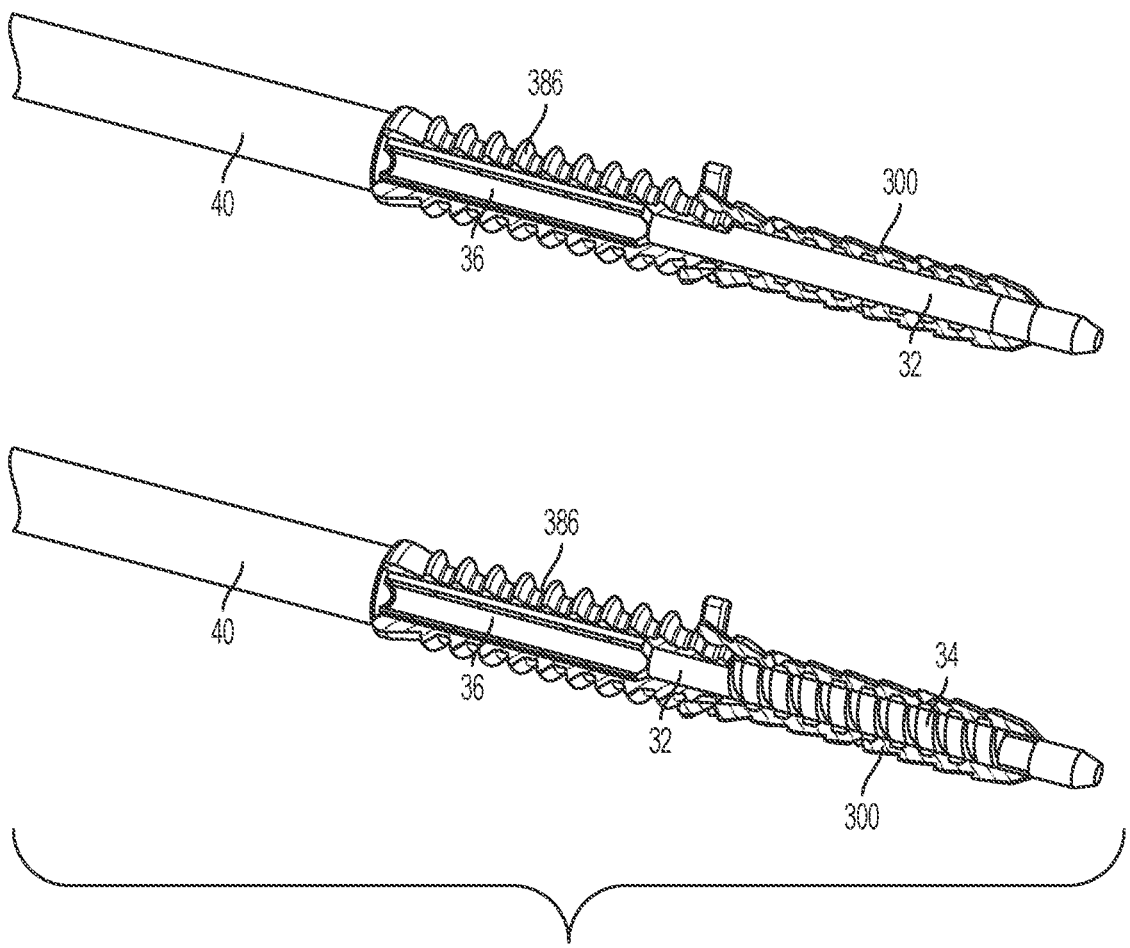
FIG. 16 depicts a cut-away view of the alternative inserter tooling coupled with the cannulated shaft of a surgical instrument.

Referring now to FIGS. 14, 15, and 16, there is shown an alternative embodiment of the surgical implementation using an alternative inserter tooling 32. Referring first to FIG. 14, there is shown an exploded view of a shaft 40 of a surgical instrument configured to receive the inserter tooling 32. The inserter tooling 32 can have a first engagement region 34 configured to engage the anchor 300. For example, the first engagement region 34 may have threads to match threads in the threaded portion 276 (FIG. 5) on the interior of the anchor 300. This configuration is beneficial because the matching threads (or the first engagement region 34, generally) provide positive engagement to facilitate insertion of the anchor 300.

The shaft 40 of a surgical instrument may be cannulated in order to receive the inserter tooling 32. The shaft 40 may have a second engagement region 36 that is configured to engage the movable element 386. This configuration may implement a tip 38 with features that match the tooling feature 296 (FIG. 9) on the movable element 386. This configuration allows the surgeon to simultaneously insert the anchor 300 and the movable element 386 into the bone tunnel permitting the surgeon to perform the surgical procedure in fewer steps.

As shown in FIG. 16, the inserter tooling 32 is received through the cannulated shaft 40 of the surgical instrument in preparation of inserting the anchor 300 into the bone tunnel 12 (FIG. 15). The first engagement region 34 engages the anchor 300. As noted above, the first engagement region may or may not have threads matching the threaded portion 276 (FIG. 5) on the interior of the anchor 300. The second engagement region 36 engages with the movable element 386. As also noted above, the second engagement region 36 may or may not utilize a tip 38 with features matching the tooling feature 296 (FIG. 9) on the movable element 386.

Referring now to FIG. 15, there is shown an elevation view of the alternative embodiment of the surgical with the anchor 300 in its un-deployed state. In this embodiment, the second engagement region 36 is engaged with the movable element 386 and the first engagement region 34 is engaged with the anchor 300. The surgeon can apply direct pressure on the shaft 40 in the direction of the bone tunnel 12. The surgeon needs only to push the anchor 300 into position between the legs 18 of the graft tissue 10. Using the shaft 40, surgeon can then rotate the movable element 386 into position in the anchor 300 (and the shaft 40 can be removed after a successful deployment).

Referring back to FIG. 13, the movable element 386 expands the anchor 300 from its first outer dimension to its second outer dimension, urging the contact surface 136 (FIG. 2) radially outward and in contact with the graft tissue 12. The radial expansion compresses the graft tissue 10 against the contact surface and the walls of the tunnel 12. As noted above, the flanged end 264 (FIG. 4) can stop (or prevent) movement of the anchoring system 384 further into the bone tunnel 10 when the flanged end 264 (FIG. 4) is at or proximate the proximal opening of the bone tunnel 12.

While embodiments of the present invention has been particularly shown and described with reference to certain exemplary embodiments, it will be understood by one skilled in the art that various changes in detail may be effected therein without departing from the spirit and scope of the invention as defined by claims that can be supported by the written description and drawings. Further, where exemplary embodiments are described with reference to a certain number of elements it will be understood that the exemplary embodiments can be practiced utilizing either less than or more than the certain number of elements.

What is claimed is:

1. An anchor, comprising:
a cylindrical body having a central longitudinal axis, a most proximal end, a most distal end and an inner surface and an outer surface, the body being formed of a plurality of integrated segments wherein a portion of the outer surface of each integrated segment of the plurality of integrated segments tapers away from the central longitudinal axis extending from the distal end to the proximal end, a most proximal end surface of each integrated segment of the plurality of integrated segments is wider than a most distal end surface of each integrated segment of the plurality of integrated segments; the inner surface defining a central bore, the cylindrical body having a slot exposing the central bore, the slot having a helical path around the central longitudinal axis and through at least one of the plurality of integrated segments that taper away from the central longitudinal axis, wherein the slot is configured to expand axially so that the cylindrical body changes from a first state to a second state in response to pressure on the inner surface, and wherein an outer diameter of the cylindrical body in the second state is larger than the outer diameter of the cylindrical body in the first state.

2. The anchor of claim 1, further comprising one or more protrusions disposed annularly around the cylindrical body.

3. The anchor of claim 1, wherein the slot traverses the cylindrical body in both a circumferential direction and a longitudinal direction.

4. The anchor of claim 1, wherein the slot has a first end and a second end, one each proximate the distal end and the proximal end, respectively, and wherein the slot makes at least one complete revolution around the central longitudinal axis between the first end and the second end.

5. The anchor of claim 1, wherein the cylindrical body comprises one or more frangible connections that are configured to retain the first state prior to pressure on the inner surface of the central bore.

* * * * *